(12) United States Patent
Silvis et al.

(10) Patent No.: US 7,565,846 B2
(45) Date of Patent: Jul. 28, 2009

(54) PARTICULATE SAMPLER AND DILUTION GAS FLOW DEVICE ARRANGEMENT FOR AN EXHAUST SAMPLING SYSTEM

(75) Inventors: William Martin Silvis, Ann Arbor, MI (US); Gerald Marek, Ann Arbor, MI (US); Wolfgang Schindler, Graz (AT)

(73) Assignee: AVL North America Inc., Plymouth, MI (US)

( * ) Notice: Subject to any disclaimer, the term of this patent is extended or adjusted under 35 U.S.C. 154(b) by 198 days.

(21) Appl. No.: 11/546,048

(22) Filed: Oct. 11, 2006

(65) Prior Publication Data
US 2008/0087107 A1    Apr. 17, 2008

(51) Int. Cl.
*G01N 1/24* (2006.01)
(52) U.S. Cl. .................................. 73/863.03
(58) Field of Classification Search .............. 73/863.02, 73/863.03, 23.32
See application file for complete search history.

(56) References Cited

U.S. PATENT DOCUMENTS

| | | | | |
|---|---|---|---|---|
| 4,361,028 A | * | 11/1982 | Kamiya et al. | 73/23.33 |
| 4,586,367 A | * | 5/1986 | Lewis | 73/23.33 |
| 5,184,501 A | * | 2/1993 | Lewis et al. | 73/23.31 |
| 5,546,788 A | * | 8/1996 | Dickow | 73/28.01 |

(Continued)

FOREIGN PATENT DOCUMENTS
WO    WO 2006/086615    8/2006

OTHER PUBLICATIONS

Wei, Qiang, "Real-Time Measuring System for Engine Exhaust Solid Particle Number Emission-Performance and Vehicle Tests," SAE Technical Paper Series, 2006-01-0865.

(Continued)

*Primary Examiner*—Hezron Williams
*Assistant Examiner*—Tamiko D Bellamy
(74) *Attorney, Agent, or Firm*—Carlson, Gaskey & Olds

(57) ABSTRACT

An exhaust sampling system is provided that includes a sampler having a sample inlet for receiving an exhaust gas sample. The sampler includes a mixer for receiving the exhaust gas sample and a diluent to produce a diluted exhaust gas. The exhaust sampling system includes first and second dilution gas flow devices. The first and second dilution gas flow devices are fluidly connected to one another at a second junction. Any diluent provided by the first and second dilution gas flow devices intermingles with one another prior to reaching the mixer. A diluted sample flow meter is arranged downstream from the mixer for receiving the diluted exhaust gas. In one example, diluent flow from the first and second dilution gas flow devices intermingles before being introduced to the mixer. In another example, diluent flow from the first dilution gas flow device is leaked out of the second dilution gas flow device in a controlled manner to achieve a desired diluent flow into the mixer. The example exhaust sampling system does not require a measurement of the flow of exhaust gas sample into the system. Instead, the flow of the diluted exhaust gas is measured by the diluted sample flow meter. And, the flow of diluent through the first and second dilution flow meters is measured and the net flow through the first and second dilution flow meters is subtracted from the flow of the diluted exhaust gas through the diluted sample flow meter.

8 Claims, 2 Drawing Sheets

U.S. PATENT DOCUMENTS

| | | | |
|---|---|---|---|
| 5,650,565 A * | 7/1997 | Nagy et al. | 73/199 |
| 6,200,819 B1 * | 3/2001 | Harvey et al. | 436/179 |
| 6,370,936 B1 * | 4/2002 | Yamagishi et al. | 73/1.35 |
| 6,460,400 B1 * | 10/2002 | Ichikawa | 73/23.31 |
| 7,404,340 B2 * | 7/2008 | Dickson et al. | 73/863.01 |
| 2002/0157482 A1 * | 10/2002 | Silvis et al. | 73/864 |
| 2002/0194936 A1 * | 12/2002 | Taylor et al. | 73/863.03 |
| 2003/0149536 A1 * | 8/2003 | Silvis et al. | 702/24 |

OTHER PUBLICATIONS

Wei, Qiang, "Real-Time Engine Exhaust Solid Particle Measurement with a Prototype Particle Counting System," 9th ETH-Conference on Combustion Generated Nanoparticles, Aug. 15, 2005.

Wei, Qiang, "Real-Time Measuring System for Engine Exhaust Solid Particle Number Emission-Design and Performance," SAE Technical Paper Series, 2006-01-0864.

Horiba, "Fast and Accurate Flow-Rate Control for Transient Testing," Jul. 24, 2006.

* cited by examiner

PARTICULATE SAMPLER AND DILUTION GAS FLOW DEVICE ARRANGEMENT FOR AN EXHAUST SAMPLING SYSTEM

BACKGROUND OF THE INVENTION

This invention relates to an exhaust sampling system that can be used to obtain diluted samples of exhaust gas to, for example, measure particulate matter.

Exhaust sampling systems are used to obtain a sample of an exhaust gas for measurement of various properties of the exhaust gas. In one example, an exhaust gas sample is obtained from the tailpipe of a vehicle's engine, and the exhaust sample is diluted to a desired dilution ratio. A typical arrangement utilizes a single dilution gas flow device to provide a diluent such as air to a mixer of the sampler, which mixes the exhaust gas sample and the diluent to form a diluted exhaust gas. A typical exhaust sampling system can achieve a dilution ratio of 50:1 while maintaining a desired accuracy.

For the above described system, the flow of diluent is controlled and measured using a single dilution gas flow device, such as a mass flow controller. The flow of diluted exhaust gas is measured using a flow meter. The flow of diluent is subtracted from the flow of diluted exhaust gas to determine the flow of the exhaust gas sample into the exhaust sampling system. The diluted exhaust gas is used, for example, to determine the amount of particulate matter within the exhaust gas. The total particulate matter produced by the vehicle's engine can be determined using the calculated flow of the exhaust gas sample into the exhaust sampling system relative to a total flow of exhaust gas produced by the vehicle's engine, which may be measured by another exhaust measurement device.

It may be desirable to obtain dilution ratios greater than 50:1. However, this is difficult to achieve using a single dilution gas flow device since the turn down ratio and resolution of the dilution gas flow device must be very high. The resolution limits the accuracy of the sample flow measured by the dilution gas flow device. That is, the dilution gas flow device must control and measure very small changes in flow it provides. To this end, exhaust sampling systems have been developed that utilize two dilution gas flow devices. In this type of system, one of the dilution gas flow devices measures diluent, which is then mixed with the exhaust gas sample. Subsequent to mixing of the diluent and the exhaust gas sample, the diluted exhaust gas is further diluted by introducing additional diluent from another dilution gas flow device. In this prior art system, the flow of the sample exhaust gas into the exhaust sampling system is measured.

Determination of sample flow by measuring the sample exhaust gas is difficult to achieve accurately due to the high temperature, change in composition and pulsating nature of the exhaust gases. Cooling the exhaust gas to obtain accurate measurement is undesirable since doing so would cause particulate matter to be deposited within the exhaust sampling system prior to its measurement.

What is needed is an exhaust sampling system that does not require a measurement of the exhaust gas sample flow into the exhaust sampling system, and is able to achieve high dilution ratios. Moreover, it is desirable to provide an exhaust sampling system that is easy to calibrate.

SUMMARY OF THE INVENTION

An exhaust sampling system is provided that includes a sampler having a sample inlet for receiving an exhaust gas sample. The exhaust sampling system includes a mixer providing a first junction for receiving the exhaust gas sample and a diluent, for example HEPA filtered air, to produce a diluted exhaust gas. The exhaust sampling system includes first and second dilution gas flow devices that respectively include first and second control valves and first and second dilution flow meters. The first and second dilution gas flow devices are fluidly connected to one another at a second junction. A diluent line fluidly interconnects the first and second junction for providing a diluent from at least one of the first and second dilution gas flow devices to the mixer. Any diluent provided by the first and second dilution gas flow devices intermingles with one another prior to reaching the mixer. A diluted sample flow meter is arranged downstream from the first junction for receiving the diluted exhaust gas.

In one example, diluent flow from the first and second dilution gas flow devices intermingles before being introduced to the mixer. In another example, some diluent flow from the first dilution gas flow device is removed by the second dilution gas flow device in a controlled manner to achieve a desired diluent flow into the mixer.

The example exhaust sampling system does not require a direct measurement of the flow of exhaust gas sample into the system. Instead, the flow of the diluted exhaust gas is measured by the diluted sample flow meter. The flow of diluent through the first and second dilution flow meters is measured and the net flow through the first and second dilution flow meters is subtracted from the flow of the diluted exhaust gas through the diluted sample flow meter.

The first dilution gas flow device and diluted sample flow meter are calibrated relative to one another. The second dilution gas flow device and/or the sample inlet can be blocked, or otherwise monitored for zero flow, during the calibration procedure. A differential pressure sensor can be used with the sampler, upstream of the mixer, to ensure that there is no flow through the sample inlet during the calibration procedure. The flow through the second dilution gas flow device and the sample inlet closely follow one another during a test procedure, in the examples.

These and other features of the present invention can be best understood from the following specification and drawings, the following of which is a brief description.

DETAILED DESCRIPTION OF THE PREFERRED EMBODIMENT

Figure 1:
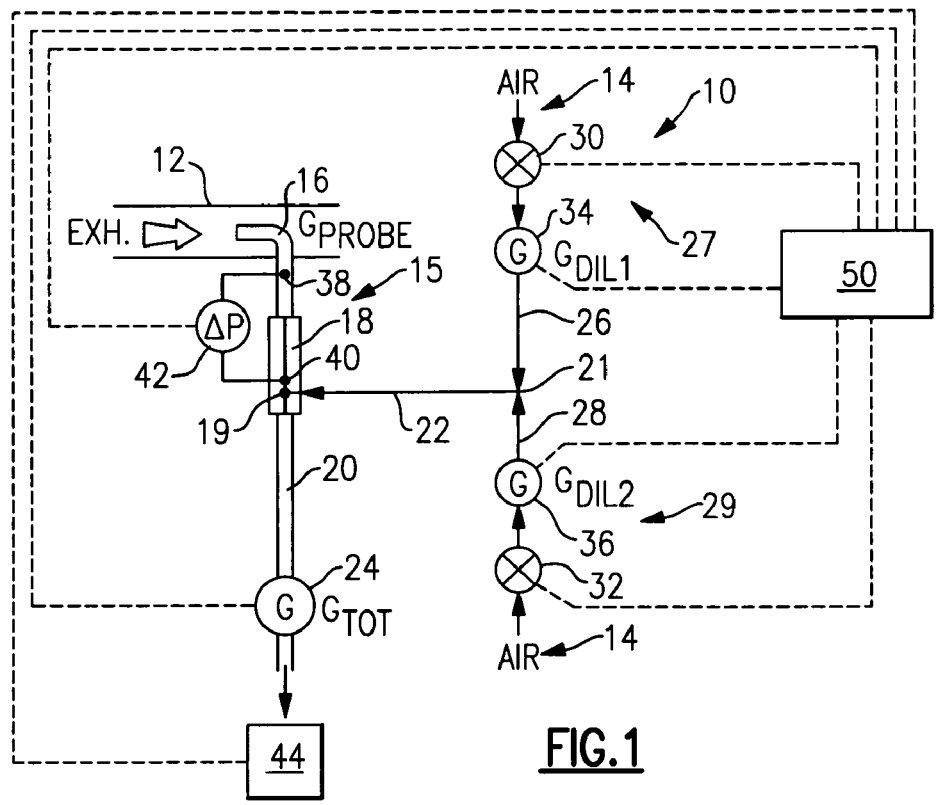
FIG. 1 is a schematic view of one example exhaust sampling system.

An exhaust sampling system 10 is schematically shown in FIG. 1. The system 10 includes an exhaust source 12, such as a tailpipe of a vehicle's engine. The exhaust source 12 may also be an exhaust measurement system that is used to measure the total volume of exhaust gas from the vehicle's engine.

A system 10 includes a sampler 15 that collects an exhaust gas sample from the exhaust source 12 using a sample inlet 16. The sampler 15 provides a mixer 18 that introduces a diluent, such as air, from a dilution source 14. The dilution source 14 is shown in two separate locations in the schematic of FIG. 1, however, the dilution source 14 can be provided by a common source. The mixer 18 provides a first junction 19 at which the exhaust gas sample and diluent are commingled with one another. Typically, a tunnel 20 is arranged downstream from the sampler 15 to enable the diluted exhaust gas to achieve a homogeneous mixture prior to subsequent operations within the system 10.

A diluent line 22 fluidly connects the first junction 19 and a second junction 21 to which first and second dilution gas flow devices 27, 29 are fluidly interconnected. In the example, the first and second dilution gas flow devices 27, 29 respectively include first and second control valves 30, 32 and first and second flow meters 34, 36. The first and second dilution gas flow devices 27, 29 can be, for example, mass flow meters. First and second lines 26, 28 extend from the second junction 21 to fluidly connect the first and second dilution flow devices 27, 29 to the second junction 21.

The first dilution gas flow device 27 outputs a flow measurement $G_{dil1}$ indicative of a diluent flow through the first dilution gas flow device 27. The second dilution gas flow device 29 outputs a diluent flow $G_{dil2}$ indicative of a diluent flow through the second dilution gas flow device 29. The net flow from the first and second dilution gas flow devices 27, 29 flows through the diluent line 22 to the mixer 18. The controller 50 may be provided by one or more pieces of software and/or hardware. A controller 50 receives the outputs $G_{dil1}$ and $G_{dil2}$, which are schematically illustrated by the dashed lines. The controller 50 also commands the first and second control valves 30, 32 (illustrated by dashed lines) to obtain a desired flow through the first and second dilution flow meters 34, 36.

A diluted sample flow meter 24 measures the flow of diluted exhaust gas downstream from the mixer 18. In one example, the diluted sample flow meter 24 can be a mixing plate or orifice. The diluted sample flow meter 24 outputs a flow $G_{tot}$ indicative of the diluted exhaust gas flow. The diluted exhaust gas can be received and processed by test equipment 44, which may include a particulate particle counter, for example. A blower (not shown) maintains a flow in the diluted sample flow meter 24, the sample inet 16 and the first and second dilution gas flow devices 27, 29.

During a test procedure using the example exhaust sampling system, the flow of the exhaust gas sample into the system 10 is not measured. Rather, the flow of exhaust gas sample is calculated by subtracting the net flow of diluent provided to the mixer 18, which is the sum of $G_{dil1}$ and $G_{dil2}$, from the diluted exhaust gas flow $G_{tot}$. In this manner, the difficulties and inaccuracies confronted when attempting to measure the exhaust sample in prior art systems is avoided. In operation, Gtot, Gdil1 and Gdil2 are flows that are set by the physical structure of the particular measuring device (e.g., an orifice) or commanded by the controller 50 (e.g., a mass flow controller). As such, the flow through the sample inlet 16 simply makes up the difference between the diluted exhaust gas flow and the diluent flow.

The system 10 shown in FIG. 1 can be calibrated, for example, by performing a relative calibration between the first dilution flow meter 34 and the diluted sample flow meter 24. In one example, a pressure lower than the exhaust line is drawn on the diluted sample flow meter 24. The diluted sample flow meter 24 is set to provide 1.5 g/s flow, for example, through the diluted sample flow meter 24.

A differential pressure sensor 42 is arranged between first and second locations 38 and 40 to ensure that there is no flow through the sampler 15 during the calibration procedure. The first and second locations 38, 40 are arranged upstream of the first junction 19. The relative calibration between the diluted sample flow meter 24 and the first dilution flow meter 34 is achieved by manipulating the first control valve 30 until the first dilution flow meter 34 reads, for example, 1.5 g/s with the differential pressure sensor 42 reading zero, which establishes that there is no flow through the sampler 15. Additionally, the second dilution line 28 can be used (due to its better adjustability) in conjunction with the differential pressure sensor 42 to adjust and define a offset between the diluted sample flow meter 24 and the first dilution flow meter 34. Optionally, a restriction, for example an orifice, can be inserted to create a larger differential pressure to assure readability of the differential pressure sensor 42. In this manner, the diluted sample flow meter 24 and first dilution flow meter 34 are calibrated relative to one another. The second dilution flow meter 36 can be calibrated on a bench relative to a reliable flow standard, as is known in the art.

The flow ranges of the first and second flow devices are selected to enable a more accurate calibration and achieve better accuracy during the test procedure. To this end, any flow measurement at the sampler has been eliminated. Instead, a simple differential pressure measurement is made for calibration purposes. The differential pressure sensor is not needed during a test procedure.

Since a relative calibration is employed between the first dilution gas flow device 27 and the diluted sample flow meter 24 in which the first dilution gas flow device 27 has a flow of, for example, 1.5 g/s to match the flow of the diluted sample flow meter 24, it is desirable that the first dilution gas flow device's operating range during a test be close to the 1.5 g/s flow during calibration. The second dilution gas flow device 29 corresponds to the flow through the sample inlet, which is a much smaller flow than the flow through the first dilution gas flow device 27. This ensures that the more accurately calibrated flow device, which is the first dilution gas flow device 27 in the example system, accounts for the majority of the flow thereby making the overall flow measurements obtained by the exhaust sampling system more accurate and reliable. This can be illustrated by an example test procedure.

Figure 3:
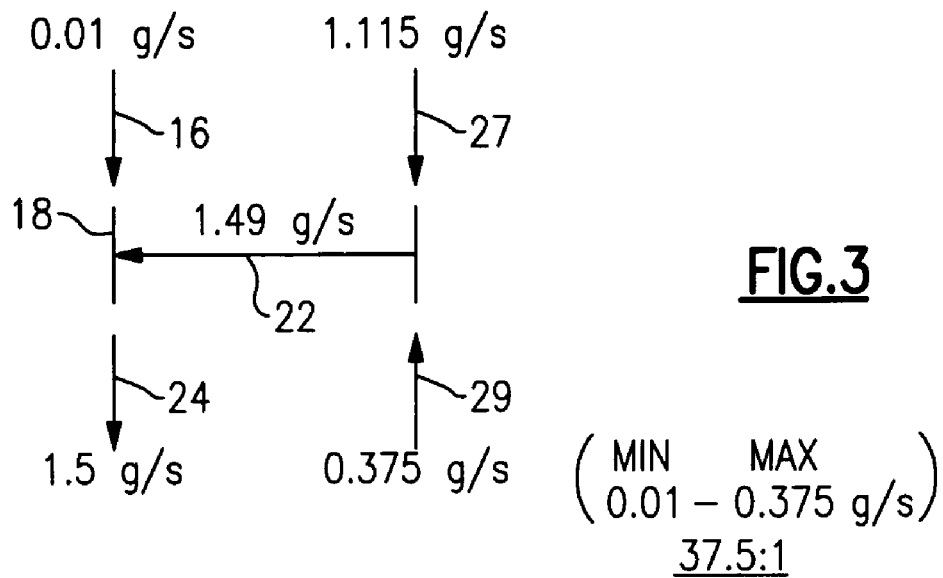
FIG. 3 is a schematic view of the exhaust sampling system shown in FIG. 1 during an minimum exhaust gas sample flow during an example test.

For exhaust sampling system shown in FIG. 1, the flow through the diluted sample flow meter might be fixed at 1.5 g/s. In one example, a desired dilution ratio is 150:1. Under some circumstances, the minimum desirable dilution ratio might be four. Accordingly, the maximum flow through the sample inlet 16 ($G_{pmax}$) permitted is 0.375 g/s (1.5 g/s/4) for the above example parameters. The minimum flow through the sample inlet 16 ($G_{pmin}$) during the test at a dilution ratio of 150:1 is 0.010 g/s (1.5/150). Flows through the exhaust sampling system 10 are shown in FIG. 3 for the minimum flow through the sample inlet 16. The relationship between the sample inlet 16, the diluted sample flow meter 24 and first and second dilution gas flow devices 27, 29 is represented by the following equations:

$$G_{tot} = G_{dil1} + G_p + G_{dil2} \quad \text{(Equation 1)}$$

$$Q = G_{tot}/G_p \quad \text{(Equation 2)}$$

In the example of a dilution ratio of 150:1, the flow into the mixer 18 through the diluent line 22 must be 1.49 g/s to achieve the 1.5 g/s flow through the diluted sample flow meter 24 (1.5 g/s-0.01 g/s). Since it is desirable to have the flow through the first dilution gas flow device 27 as close to the 1.5 g/s calibration flow as possible, the first dilution gas flow device is commanded to 1.115 g/s using the first control valve 30. The flow from the second dilution flow meter 36 must, when combined with the flow of the first dilution flow meter 34, equal the needed diluent flow into the mixer 18, which is 1.49 g/s. The second dilution flow meter 36 is set to 0.375 g/s so that the flow of the exhaust gas sample into the system will be 0.01 g/s at the minimum exhaust gas sample flow rate in the example.

For the above example, the second dilution gas flow device 29 operates at a 37.5:1 turn down ratio (0.01 g/s at $G_{pmin}$-0.375 g/s at $G_{pmax}$). These turn down ratios are well within the typical 50:1 turn down ratios of current systems and thus able to control flows with desired accuracy.

Figure 2:
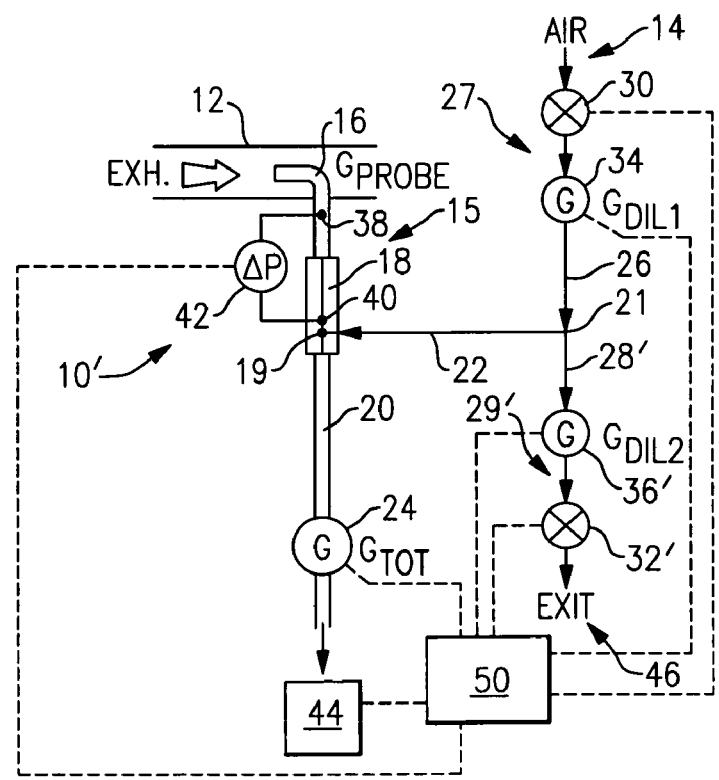
FIG. 2 is a schematic view of another example exhaust sampling system.

Another example exhaust sampling system 10' is shown in FIG. 2. However, diluent is permitted to escape the exhaust sampling system 10' in a controlled manner through an exit 46 rather than entering the system, as is the case in FIG. 1. The arrangement in FIG. 2 can simplify calibration and operation of the system as compared to the system illustrated in FIG. 1, which will be appreciated from the discussion below.

Figure 4:
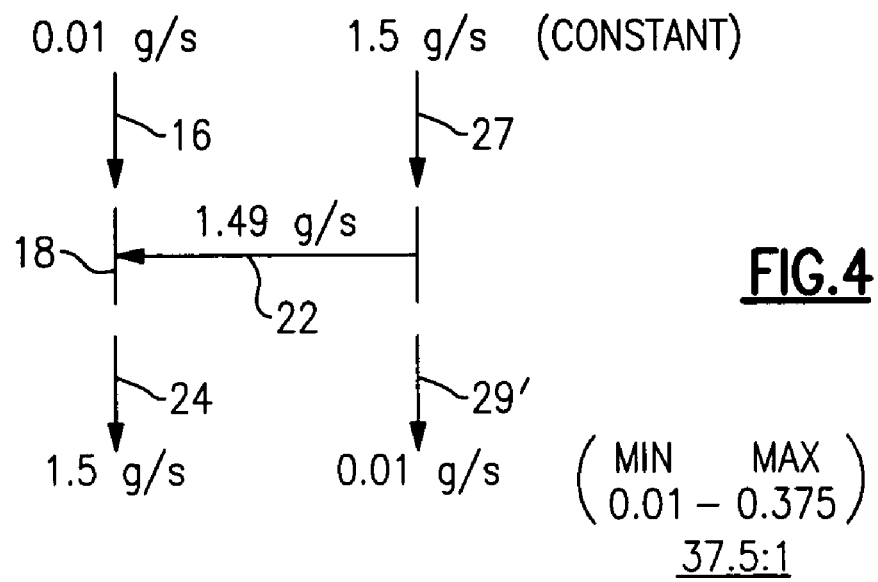
FIG. 4 is a schematic view of the exhaust sampling system shown in FIG. 2 during a minimum exhaust gas sample flow during an example test.

During a test procedure, $G_{dil1}$ is set to $G_{tot}$. In the example, $G_{tot}$ and $G_{dil1}$ are both 1.5 g/s. Since the flow through the first dilution flow meter 34 is constant during the test, the flow does not deviate from the calibrated flow which could contribute to inaccuracy. Gdil2, then, corresponds with the flow through the sample inlet 16, which in the example is 0.01 g/s. This relationship between the sample flow meter 24, the sample inlet 16 and the first and second dilution gas flow devices 27, 29' is represented in FIG. 4 and is represented by the equation below.

$$G_{tot}=G_{dil1}+G_p-G_{dil2} \quad \text{(Equation 3)}$$

The exhaust sampling system 10' can calibrated in the same manner as described above relative to the exhaust sampling system 10.

Although a several example embodiments of this invention have been disclosed, a worker of ordinary skill in this art would recognize that certain modifications would come within the scope of this invention. the following claims should be studied to determine the true scope and content of this invention.

What is claimed is:

1. An exhaust sampling system comprising:
 a sampler including a sample inlet for receiving an exhaust gas sample;
 a mixer providing a first junction for receiving the exhaust gas sample and a diluent to produce a diluted exhaust gas;
 first and second dilution gas flow devices are fluidly connected in parallel relative to one another at a second junction, and a diluent line fluidly interconnecting the first and second junctions for providing a diluent from at least one of the first and second dilution gas flow devices to the mixer; and
 a diluted sample flow meter downstream from the first junction for receiving the diluted exhaust gas.

2. The exhaust sampling system according to claim 1, wherein the first and second dilution gas flow devices respectively include first and second control valves and first and second dilution flow meters, and a controller reading the first and second flow meters and commanding the first and second controllers to achieve a desired diluent flow through each of the first and second flow meters.

3. The exhaust sampling system according to claim 1, wherein the second junction receives diluent from the first and second dilution gas flow devices.

4. An exhaust sampling system comprising:
 a sampler including a sample inlet for receiving an exhaust gas sample;
 a mixer providing a first junction for receiving the exhaust gas sample and a diluent to produce a diluted exhaust gas;
 first and second dilution gas flow devices are fluidly connected to one another at a second junction, and a diluent line fluidly interconnecting the first and second junctions for providing a diluent from at least one of the first and second dilution gas flow devices to the mixer, wherein the second junction receives diluent from the first and second dilution gas flow devices;
 a diluted sample flow meter downstream from the first junction for receiving the diluted exhaust gas; and
 wherein the flow of diluent through the second dilution gas flow device corresponds to the flow of the exhaust gas sample through the sample inlet, additionally, the flow of diluent through the first dilution gas flow device is the difference between the flow of diluted exhaust gas through the diluted sample flow meter and the flow of diluent through the second dilution gas flow device and the flow through the sample inlet.

5. An exhaust sampling system comprising:
 a sampler including a sample inlet for receiving an exhaust gas sample;
 a mixer providing a first junction for receiving the exhaust gas sample and a diluent to produce a diluted exhaust gas;
 first and second dilution gas flow devices are fluidly connected to one another at a second junction, and a diluent line fluidly interconnecting the first and second junctions for providing a diluent from at least one of the first and second dilution gas flow devices to the mixer;
 a diluted sample flow meter downstream from the first junction for receiving the diluted exhaust gas; and
 wherein the first dilution gas flow device provides a diluent to the second junction and the second dilution gas flow device removes a portion of the diluent from the second junction prior to the diluent reaching the mixer.

6. The exhaust sampling system according to claim 5, wherein the flow of diluent through the first dilution gas flow device equals the flow of diluted exhaust gas through the diluted sample flow meter, and the flow through the second dilution gas flow device corresponds to the flow of the exhaust gas sample through the sample inlet.

7. An exhaust sampling system comprising:
 a sampler including a sample inlet for receiving an exhaust gas sample;
 a mixer providing a first junction for receiving the exhaust gas sample and a diluent to produce a diluted exhaust gas;
 first and second dilution gas flow devices are fluidly connected to one another at a second junction, and a diluent line fluidly interconnecting the first and second junctions for providing a diluent from at least one of the first and second dilution gas flow devices to the mixer;
 a diluted sample flow meter downstream from the first junction for receiving the diluted exhaust gas; and
 wherein a differential pressure sensor is in fluid communication with the sample inlet and arranged upstream from the mixer, the differential pressure sensor detecting a zero differential pressure during a calibration procedure to confirm there is no flow through the sample inlet.

8. The exhaust sampling system according to claim 1, wherein the first and second dilution gas flow devices are mass flow controllers.

* * * * *